United States Patent [19]

Senju et al.

[11] 4,073,689

[45] Feb. 14, 1978

[54] METHOD FOR IMMOBILIZING ENZYME

[75] Inventors: Ryoichi Senju, 41-18, Higashiwakahisa, Minami, Fukuoka, Fukuoka, Japan; Hiroo Tanaka, Fukuoka, Japan

[73] Assignee: Ryoichi Senju, Japan

[21] Appl. No.: 795,133

[22] Filed: May 9, 1977

Related U.S. Application Data

[63] Continuation of Ser. No. 653,261, Jan. 28, 1976, abandoned.

[51] Int. Cl.² ............................................. C07G 7/02
[52] U.S. Cl. ...................................... 195/63; 195/68; 195/DIG. 11

[58] Field of Search .................... 195/63, 68, DIG. 11; 260/112 R

[56] References Cited

U.S. PATENT DOCUMENTS 3,956,113  5/1976  Brenner ............................ 195/68 X

*Primary Examiner*—Lionel M. Shapiro
*Attorney, Agent, or Firm*—Fitzpatrick, Cella, Harper & Scinto

[57] ABSTRACT

A stable immobilized enzyme is obtained by reacting an enzyme with a substance having an N-halogenoamide group in a weak alkaline aqueous solution.

11 Claims, No Drawings

METHOD FOR IMMOBILIZING ENZYME

This is a continuation of application Ser. No. 653,261, filed Jan. 28, 1976, now abandoned.

BACKGROUND OF THE INVENTION

This invention relates to a method for immobilizing an enzyme utilizing the specific chemical reactivity of N-halogenoamide group.

Advantages of using an enzyme after immobilization are as follows. First of all, reusing of the enzyme is possible. Secondly, it is possible to carry out a continuous enzymatic reaction in a column. Thirdly, delicate control of a reaction is possible, since it is easy to separate reaction products from the enzyme. The fourth advantage is to be able to avoid various troubles due to contamination of final products with the enzyme or impurities. Further, the stability of the enzyme is increased and consequently the enzyme is easy to utilize. Lastly, it is possible to automatically carry out the enzymatic reaction and consequently to reduce the cost for production. Thus the immobilization of an enzyme has various advantages. Many attempts have so far been made to utilize enzymes after immobilization and the methods for immobilization can be classified mainly into adsorption process, inclusion process and chemical bonding process.

The adsorption process comprises adsorbing enzymes onto the surface of an insoluble solid and immobilizing the enzymes. Its operation is simple, but the adsorbability is so weak that the adsorbed enzymes are liable to be desorbed when there are salts or substrates at high concentrations. Therefore, the adsorption process is not satisfactory in view of the essential object of the immobilization. That is, the adsorption process is applicable only when carriers have an especially strong affinity for the enzyme molecules. At present, diethylaminoethyl cellulose is used as the carrier.

In the inclusion process, enzymes are contained into polymeric gels. At present, gels of copolymers of acrylamide and N,N'-methylene-bis-acrylamide are used. Since the enzymes themselves are not chemically bonded to polymers forming the gels, the enzymes are liable to flow out if lattice size of the gels is too large. However, if the lattice size is made smaller, the rate of enzymatic reaction becomes lower. Therefore, it is an important task to adjust the lattice size.

In the chemical bonding process, enzyme molecules are immobilized to the surface of a carrier by chemical covalent bonds utilizing functional groups of the enzyme molecules. Though the degree of activity of the enzymes is slightly lowered owing to the accompanying chemical reaction, the stability of the enzymes is excellent and the loss due to washing is small. Therefore, the chemical bonding process is most effective as a method for immobilizing the enzyme. However, the process still has many problems to be solved. That is, complicated steps and expensive reagents are necessary for chemically bonding the enzyme molecules to the surface of a carrier and also severe reaction conditions are often required. From the viewpoint of reaction forms, the processes now employed can be classified mainly into the following four procedures; (A) procedure of forming peptide bonds, (B) procedure of alkylation, (C) procedure of diazo coupling, and (D) procedure of forming Schiff's base. As the procedure (A), there may be mentioned a procedure comprising converting the carrier to azide, isocyanate, carbodiimide or iminocarbonate, and then reacting the resulting derivative with amino groups of the enzymes. As the procedure (B), there may be mentioned a procedure wherein hydroxyl groups of cellulose are activated using cyanur chloride.

As the procedure (D), there may be mentioned a procedure comprising bonding aminoalkylsilane to the surfaces of porous glass granules and then forming Schiff's salt using glutaraldehyde. However, since the formation of the Schiff's salt is an equilibrium reaction, there is a disadvantage that the enzymes are gradually released as in the adsorption process.

In the conventional processes, anyway, complicated steps, expensive reagents and strict reaction conditions are necessary for activating the carrier.

The present inventors have studied a method of immobilizing enzyme by treating the enzyme with an N-halogenoamide compound.

It is well known that the N-halogenoamide compound is formed as an intermediate compound in the Hofmann's decomposition of acid amide. That is, when an amide compound is reacted with a hypohalogenoxyacid ions ($OX^-$) under strong alkalinity, an amine is formed through an N-halogenoamide compound as shown in the following formula:

$$R-CONH_2 \xrightarrow{OX^-} R-CONHX \xrightarrow{\text{Strong alkali}} R-NH_2$$

As to the Hofmann's decomposition, many researches have been made on the relation between the chemical structures of amide compounds and amine yields. However, no research has yet been reported as to the chemical reactivity of an N-halogenoamide compound, a reaction intermediate, in aqueous solution thereof.

The present inventors have made studies on N-halogenation reaction of various amides, and have found that an N-halogenoamide group has a low rate of conversion to the amino group under weak alkalinity and rather reacts with atomic groups containing active hydrogen, for example, $-NH_2$, $-OH$, $-CONH_2$, etc., to form ureide, urethane, and acylurea, respectively.

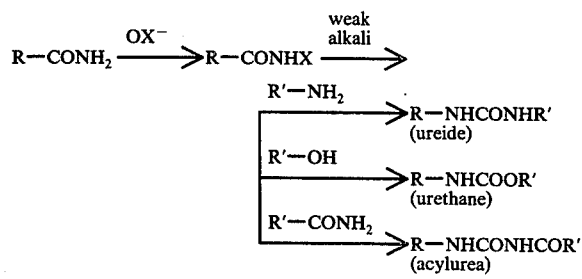

It has been found that the N-halogenoamide group is especially active upon the amino group and is very reactive even under mild reaction conditions such as pH 8 - 9 and reaction temperature of 30° - 40° C.

SUMMARY OF THE INVENTION

In accordance with the present invention, a stable immobilized enzyme is obtained by reacting an enzyme with a substance having an N-halogenoamide group in a weak alkaline aqueous solution.

DETAILED EXPLANATION OF THE INVENTION

As the substance having an N-halogenoamide group in the present invention, water-soluble, low molecular weight, multi-valent halogenoamide compounds (hereinafter referred to as Substance A), water-soluble, high-molecular weight, multi-valent halogenoamide compounds (hereinafter referred to as Substance B) and solid carriers having an N-halogenoamide group (hereinafter referred to as Substance C) are used. Substances A, B and C are prepared in the following manners respectively.

Preparation of Substance A

Substance A is prepared by N-halogenating multi-valent amide compounds such as polycarboxylic acid amide, for example, adipic acid amide and succinic acid amide; carbamoylized polyhydric alcohols, carbamoylized sugars, etc.

As the polyhydric alcohol to be carbamoylized, glycerin, polyethylene glycol, polypropylene glycol, etc., may be used. As the sugar to be carbamoylized, glucose, fructose, sucrose, pentaerythritol, sorbitol, mannitol, etc., may be used.

The halogenation reaction may be carried out according to any known method. For example, the N-halogenoamide compound is prepared by reacting an amide compound with a hypohalogenite such as sodium hypochlorite at a temperature of $-10°$ – $50°$ C.

The carbamoylization reaction may be carried out according to any known method. For example, the carbamoylized polyalcohols or sugars are prepared by reacting polyalcohols or sugars with acrylonitrile and then by reacting the resultant mixture with hydrogen peroxide.

Preparation of Substance B

Substance B used in the present invention is prepared by carbamoylizing water-soluble multi-valent alcohols and then by halogenating them according to the method of the above-described halogenation reaction.

As the multi-valent alcohols, cellulose, starch, agar, alginic acid, Knojak (devil's-tongue jelly), polyvinyl alcohols, etc., may be used. Further, homopolymers and graft polymers of acrylamide or methacrylamide, or their copolymers with other polymerizable vinylpolymers, etc., are useful as the carbamoyl compounds.

Preparation of Substance C

The solid carrier having a halogenoamide group is prepared by carbamoylizing and halogenating a suitable solid material.

As the material, any material capable of being carbamoylized, irrespective of natural or synthetic origin, may be used. For example, cellulose, wood materials such as pulp, etc. wool, silk, cotton, polymeric materials such as nylon, polyvinylalcohol, weakly basic anion exchange resin such as Diaion CR-20 (trade name, produced by Mitsubishi Chemical Industries Ltd.) may be used.

The solid material may be used in any desired form, such as powdery, granular, fibrous, fabric, membrane paper, plate form, etc. An especially preferable carrier is hydrophilic and porous, but not rigid, because the enzymatic reaction is generally carried out in an aqueous solution of the enzyme and the hydrophilic carrier does not impair diffusion of the substrate and mutual action of the substrate and the carrier. Higher stability of the immobilized enzyme can be obtained with a more hydrophilic carrier. Further, by using a porous carrier, the surface area of the carrier becomes larger, and the amount of the enzymes to be bonded is increased. Furthermore, as to the rigidity of the carrier, rather a soft carrier such as cellulose is preferred to a rigid carrier such as glass in order to prevent deformation of the enzyme molecules and also to obtain high stability of the enzyme.

The reaction of immobilizing enzymes with the substances having an N-halogenoamide group is carried out at a temperature of $-10°$ – $50°$ C, preferably, $15°$ – $40°$ C and at a pH of 8 – 11 in an aqueous solution of the enzyme.

The N-halogenoamide group of the substances undergoes crosslinking reaction with the amino group of the enzyme to immobilize the enzyme.

When Substance B is used, the N-halogenoamide group reacts with the amino groups partially by-produced by Hofmann's decomposition and undergoes crosslinking reaction between the molecules as shown below, thereby self-condensation and gelation of the N-halogenoamide group are effected.

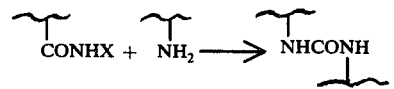

At the same time, the N-halogenoamide group of the N-halogenoamide compound reacts with an amino group of an enzyme.

Therefore, in this case, the enzyme is immobilized physically and chemically.

The strength of the gel and the lattice size can be varied by adjusting the kind of the polymeric multi-valent halogeno amide, its concentration and density of halogenoamide groups.

Enzymes which may be immobilized in the process of the present invention include purified or crude enzymes, enzyme mixtures and enzyme systems present in or isolated from animal, plant or microbial tissue. They are used in the form of whole cells, intact intracellular particles and crude extracts of these tissues.

For example, proteolytic enzymes such as trypsin, chymotrypsin and papain; hydrolases such as $\alpha$-amylase invertase, $\beta$-galactosidase, ribonuclease, alkaline phosphatase, amyloglucosidase and dextranase; dehydrogenases such as creatine phosphokinase and pyruvate kinase; oxidases such as glycose oxidase and amidases such as amidase and penicillin amidases may be used.

The concentration of the enzyme solution used in the present method is not limited, but 0.01 – 10% enzyme solution is preferably used.

In immobilizing an enzyme according to the process of the present invention, the loss of the enzyme is very small since the immobilizing reaction is carried out in an aqueous solution of the enzyme under very mild reaction conditions.

The immobilized enzyme obtained according to the method of the present invention is very stable against washing. For example, the $\alpha$-amylase immobilized through covalent bondage with N-chlorocarbamoylethyl pulp, which has been prepared by carbamoylethylizing pulp and then N-chlorinating the resulting carbamoylethylized pulp, shows an excellent stability against washing as shown in Table 1 of Example 3.

For comparison, the stability of the α-amylase immobilized through adsorption on the cation pulp prepared from the same pulp material is also shown in Table 1.

The present invention is further illustrated with reference to the following representative examples.

EXAMPLE 1

One hundred forty ml of 1.0% aqueous solution of sodium hydroxide and 5.3 g (0.1 mole) of acrylonitrile (AN) are added to 21 g (0.1 mole) of commercially available hydroxyethylcellulose (HEC) and the mixture is allowed to react at 50° C for 60 minutes with stirring. Then, 23 g (0.2 mole) of 30% solution of hydrogen peroxide is added thereto in two or three portions, and the solution is allowed to react at 20° C for 90 minutes. The reaction steps are illustrated by the following formula:

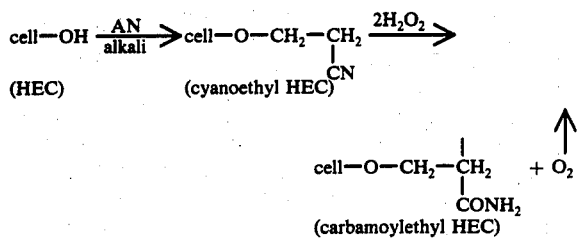

The resulting aqueous solution of carbamoylethyl HEC is diluted to twice the volume with water. To the 10.0 g (0.0027 mole as the carbamoyl group) of dilute carbamoylethyl HEC solution is added 2.7 ml (0.0027 mole) of 1M aqueous solution of sodium hypochlorite. The mixture is subjected to N-chlorination at 0° - 2° C for 60 minutes and then neutralized to pH about 9 with 1N acetic acid. To the resulting solution is added 2.0 ml of 250 mg/100 ml aqueous solution of α-amylase. Then, the mixture is sufficiently stirred, slowly heated up to 30° C and is allowed to stand for 20 minutes to obtain α-amylase immobilized in the gel of carbamoylethyl HEC. The enzyme immobilized in the gel is immobilized to the HEC chains not only by physical but also by chemical bond and therefore, will not flow out even by repeated washings.

EXAMPLE 2

To 10.0 g (0.007 mole) of 5% aqueous solution of polyacrylamide is added 2.8 ml (0.0056 mole) of 2M aqueous solution of sodium hypochlorite. The resulting mixture is subjected to N-chlorination at −5° - 0° C for 30 minutes and then neutralized to pH about 9 with 1N acetic acid. Then, 2.0 ml of 250 mg/100 ml aqueous solution of α-amylase is added thereto. After sufficient stirring, the resulting mixture is slowly heated up to 30° C and is allowed to stand for 20 minutes to obtain α-amylase immobilized in the gel of polyacrylamide. The enzyme immobilized in the gel is immobilized to the polyacrylamide chains not only by physical but also by chemical bond and therefore, will not flow out even by repeated washings.

EXAMPLE 3

Five point zero grams of acrylonitrile is dissolved in 250 ml of 0.5% aqueous solution of sodium hydroxide and 16.2 g (0.1 mole) of pulp is dipped in the resulting solution. The mixture is allowed to react at 50° C for 2 hours. Then, the reaction mixture is filtered and the residue is washed with water and dipped in 200 ml of 0.5% aqueous solution of sodium hydroxide added with 5.0 ml of 30% solution of hydrogen peroxide. The mixture is allowed to react at 20° C for 60 minutes. Then, the reaction mixture is filtered and the residue is washed with water to obtain carbamoylethyl pulp. 1.0 g of the thus obtained carbamoylethyl pulp is dispersed in 100 ml of water. 2.0 ml of 1M aqueous solution of sodium hypochlorite is added thereto and the mixture is subjected to N-chlorination reaction at 0° - 2° C for 30 minutes. After the reaction is complete, the pulp is sufficiently washed with ice water and then dipped in 100 ml of 0.1M calcium acetate buffer solution (pH 8.10) containing 100 mg of α-amylase. The mixture is allowed to react at 40° C for 3 hours to immobilize the enzyme. Table 1 shows the results of determining a resistance of the activity of the thus immobilized enzyme to washing (test 1).

The enzyme activity is expressed by the weight (mg) of amylase that is, the volume (ml) of 0.1% amylase that has lowered a blue iodine color (Blue value) by 10% at 30° C in 30 minutes.

Washing is carried out by vigorously stirring 100 mg of the immobilized enzyme in 150 ml of 0.1M calcium acetate buffer solution at 30° C for 30 minutes.

For comparison, the resistance of the enzyme immobilized by an adsorption process using cation pulp is also shown in Table 1 (test 2). The cation pulp is prepared by N-chlorinating the carbamoylethyl pulp in the way described above and then chemically bonding polyethylene imine (degree of polymerization: 100) thereto.

The activity of the enzyme immobilized according to the process of the present invention is not lowered even by repeated washings.

Table 1

| Number of washing | Enzyme activity (mg) | |
| --- | --- | --- |
| | test 1 | test 2 |
| 0 | 300 | 470 |
| 1 | 260 | 390 |
| 2 | 255 | 330 |
| 3 | 255 | 280 |
| 4 | 255 | 240 |
| 10 | 255 | 148 |

EXAMPLE 4

To 1.44 g (10 mmoles) of adipic acid amide are added 50 ml of water and 10 ml (20 mmoles) of 2M aqueous solution of sodium hypochlorite. The mixture is subjected to N-chlorination reaction for 60 minutes under ice cooling. To the reaction mixture is added 1.2 g (20 mmoles) of acetone and then the resulting solution is adjusted to pH about 9.0 with acetic acid. To the resulting solution is added 30 ml of 1% enzyme solution (α-amylase, papain, trypsin or invertase). The solution is kept at 18° C for 50 minutes to precipitate the immobilized enzyme. The activity of the resulting immobilized enzyme is not lowered even by repeated washings.

EXAMPLE 5

6.8 g (0.05 mole) of pentaerythritol, 10.6 (2 moles) of acrylonitrile, and 0.4 g of sodium hydroxide are added to 7.0 ml of water. The mixture is kept at 50° C for 60 minutes, and transferred into a separate funnel to obtain oily matter in the under layer. The oily matter is hydrolyzed by 100 g (0.88 mole) of 30% solution of hydrogen peroxide in 0.1N sodium hydroxide solution at 20° C for 3 hours. By adding acetone to the reaction mixture, 16.8 g of tetracarbamoylethylpentaerythritol is obtained (yield: 80%).

To 4.2 g (10 mmoles) of the thus obtained product are added 50 ml of water and 10 ml of 2M aqueous solution of sodium hypochlorite. The mixture is subjected to N-chlorination for 60 minutes under ice cooling, and then 1.2 g (20 mmoles) of acetone is added thereto. Then, the mixture is adjusted to pH about 9.0 with acetic acid and is added to 100 ml of 0.1M calcium acetate buffer solution (pH 8.10) containing 100 mg of α-amylase. The mixture is allowed to react at 25° C for 50 minutes to obtain the immobilized α-amylase as the white precipitate. The activity of the resulting immobilized α-amylase is not lowered even by repeated washings.

EXAMPLE 6

To 2 g of cellulose pulp are added 70 ml of water 187 mg of cerium nitrate, 0.7 ml of 1N nitric acid and 0.5 g of acrylamide. After freezing and deaeration, replacement of nitrogen gas is carried out twice and the mixture is subjected to graft polymerization at 35° C for 10 minutes. By removing homopolymers of acylamide by water washing, cellulose pulp having an acrylamide grafting ratio of 7.9% is obtained.

To 1 g of the obtained graft polymer is added 100 ml of 0.5M aqueous solution of sodium hypochlorite. The mixture is subjected to N-chlorination for 30 minutes under ice cooling and then washed four times with 10% aqueous solution of sodium chloride cooled to 0° C. Then, the resulting polymer is dipped in 100 ml of 0.1M calcium acetate buffer solution (pH 8.10) containing 100 mg of α-amylase. The mixture is allowed to react at 20° C for 60 minutes, whereby the enzyme can be immobilized to the cellulose pulp. The activity of the resulting immobilized enzyme is not lowered even by repeated washings.

EXAMPLE 7

To 6.46 g (20 mmoles) of Diaion CR-20, (weakly basic anion exchange resin) are added 14.0 g (200 mmoles) of acrylamide and 20 ml of 0.1N sodium hydroxide. The mixture is kept at 40° C for 2 hours to carbamoylethylize the amino groups of the resin. By removing the unreacted acrylamide by water washing, 8.40 g of carbamoylethylized anion exchange resin is obtained (yield: 100%).

To 1.0 g of the obtained carbomoylethylized anion exchange resin is added 10 ml of 0.5M aqueous solution of sodium hypochlorite. The mixture is subjected to N-chlorination for 60 minutes under ice cooling. After the reaction is complete, the resin is sufficiently washed with ice water and then dipped in 100 ml of 0.1M calcium acetate buffer solution (pH 8.10) containing 100 mg of α-amylase. The mixture is allowed to react at 40° C for 3 hours, whereby the enzyme can be immobilized to the granular resin. The activity of the resulting immobilized enzyme is not lowered even by repeated washings.

What is claimed is:

1. A method for immobilizing an enzyme which comprises reacting an enzyme with a compound or material having multi-valent halogenoamide groups obtained by reacting
    a. a polycarboxylic acid amide,
    b. a water-soluble multi-valent amide compound obtained by carbamoylizing polyhydric alcohols, sugars or water-soluble multi-valent alcohols having high molecular weight, or
    c. a carbamoylized solid carrier having amide groups
with a hypohalogenite in an alkaline medium.

2. A method according to claim 1, wherein said carbamoylization reaction is carried out by using acrylonitrile and hydrogen peroxide.

3. A method according to claim 1, wherein said polycarboxylic acid amide is selected from the group consisting of acrylamide and methacrylamide.

4. A method according to claim 1, wherein said polycarboxylic acid amide is selected from the group consisting of adipic acid amide and succinic acid amide.

5. A method according to claim 1, wherein said polyhydric alcohol is selected from the group consisting of glycerin, polyethylene glycol and polypropylene glycol; said multi-valent alcohol is selected from the group consisting of cellulose, starch, agar, alginic acid, Konjak and polyvinyl alcohol; and said sugar is selected from the group consisting of glucose, fructose, sucrose, pentaerythritol, sorbitol and mannitol.

6. A method according to claim 1, wherein said solid carrier is pulp, wool, silk, cotton, nylon or weakly basic annion exchange resin.

7. The method according to claim 1, wherein said enzyme is α-amylase, papain, trypsin or invertase.

8. The method according to claim 1, wherein said substance is a compound having a chloramide group.

9. The method according to claim 1, wherein said reaction is carried out at a pH of 7 - 11.

10. The method according to claim 9, wherein said reaction is carried out at a temperature of −10° - 50° C.

11. An immobilized enzyme produced by the method according to claim 1.

* * * * *